US010940049B2

United States Patent
Heinecke et al.

(10) Patent No.: US 10,940,049 B2
(45) Date of Patent: Mar. 9, 2021

(54) CONFORMABLE MEDICAL DRESSING

(71) Applicant: 3M INNOVATIVE PROPERTIES COMPANY, Saint Paul, MN (US)

(72) Inventors: Steven B. Heinecke, New Richmond, WI (US); Donald G. Peterson, Shoreview, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 667 days.

(21) Appl. No.: 14/773,956

(22) PCT Filed: Mar. 5, 2014

(86) PCT No.: PCT/US2014/020524
§ 371 (c)(1),
(2) Date: Sep. 9, 2015

(87) PCT Pub. No.: WO2014/149718
PCT Pub. Date: Sep. 25, 2014

(65) Prior Publication Data
US 2016/0015570 A1    Jan. 21, 2016

Related U.S. Application Data

(60) Provisional application No. 61/775,805, filed on Mar. 11, 2013.

(51) Int. Cl.
*A61F 13/02* (2006.01)
(52) U.S. Cl.
CPC ........ *A61F 13/0236* (2013.01); *A61F 13/023* (2013.01); *A61F 13/0243* (2013.01)

(58) Field of Classification Search
CPC ............ A61F 2013/00868; A61F 13/02; A61F 13/023; A61F 13/0236; A61F 13/0243; A61F 2013/00582; A61F 2013/00259; A61F 13/0259; A61F 13/00085; A61F 13/0203; A61L 15/26; A61L 15/58; A61L 15/46; A61L 31/16; A61L 2300/404; A61M 25/02; A61M 25/0111; A61M 2025/0273
See application file for complete search history.

(56) References Cited

U.S. PATENT DOCUMENTS

RE2,490 E    3/1842  Adams
3,389,827 A  6/1968  Abere
(Continued)

FOREIGN PATENT DOCUMENTS

CN    1976655    6/2007
CN    101500520  8/2007
(Continued)

OTHER PUBLICATIONS

International Search report for PCT International Application No. PCT/US2014/020524 dated May 12, 2014, 3 pages.

*Primary Examiner* — Ophelia A Hawthorne
(74) *Attorney, Agent, or Firm* — 3M Innovative Properties Company; Trisha D. Adamson

(57) ABSTRACT

A medical dressing that is highly flexible and conformable over skin, while maintaining strong adhesive securement to skin over extended periods of time. The dressing comprises a backing layer, support material, and a plurality of specifically placed slits in the support material, which allow for stretching and recovery of the backing layer.

19 Claims, 2 Drawing Sheets

(56) References Cited

U.S. PATENT DOCUMENTS

| | | |
|---|---|---|
| 3,645,835 A | 2/1972 | Hodgson |
| 4,112,213 A | 9/1978 | Waldman |
| 4,310,509 A | 1/1982 | Berglund |
| 4,323,557 A | 4/1982 | Rosso |
| 4,472,480 A | 9/1984 | Olson |
| 4,595,001 A | 6/1986 | Potter |
| 4,600,001 A | 7/1986 | Gilman |
| 4,737,410 A | 4/1988 | Kantner |
| 4,867,150 A | 9/1989 | Gilbert |
| 5,052,381 A * | 10/1991 | Gilbert ................ A61F 13/023 206/441 |
| 5,088,483 A | 2/1992 | Heinecke |
| 5,160,315 A | 11/1992 | Heinecke |
| 5,230,701 A | 7/1993 | Meyer |
| 5,520,629 A | 5/1996 | Heinecke |
| 5,616,387 A | 4/1997 | Augst |
| 5,622,711 A | 4/1997 | Chen |
| 5,633,010 A | 5/1997 | Chen |
| 6,383,958 B1 | 5/2002 | Swanson |
| 6,685,682 B1 | 2/2004 | Heinecke |
| 6,893,655 B2 | 5/2005 | Flanigan |
| 6,994,904 B2 | 2/2006 | Joseph |
| 7,294,752 B1 | 11/2007 | Propp |
| 7,858,838 B2 * | 12/2010 | Holm ................ A61F 13/0226 602/42 |
| 2004/0162512 A1 | 8/2004 | Liedtke |
| 2006/0002988 A1 | 1/2006 | Ellefson |
| 2007/0049859 A1 | 3/2007 | Propp |
| 2010/0106121 A1 | 4/2010 | Holm |

FOREIGN PATENT DOCUMENTS

| | | |
|---|---|---|
| WO | WO 2008/019310 | 2/2008 |
| WO | WO 2010-056541 | 5/2010 |
| WO | WO 2010-056543 | 5/2010 |
| WO | WO 2012-150235 | 11/2012 |
| WO | WO 2013-007973 | 1/2013 |
| WO | WO 2014-003957 | 1/2014 |

\* cited by examiner

CONFORMABLE MEDICAL DRESSING

CROSS REFERENCE TO RELATED APPLICATIONS

This application is a national stage filing under 35 U.S.C. 371 of PCT/US2014/020524, filed Mar. 5, 2014, which claims priority to U.S. Provisional Application No. 61/775,805, filed Mar. 11, 2013, the disclosures of which are incorporated by reference in their entirety herein.

FIELD

The present disclosure relates to a conformable medical dressing comprising a backing layer and a support layer that comprises a plurality of slits for enabling better elasticity.

BACKGROUND

Transparent film dressings are widely used as protective layers over wounds because they facilitate healing in a moist environment while acting as a barrier to contaminating liquids and bacteria. The films are also used as surgical drapes because of their barrier properties. Dressings and drapes fitting the above description are available under a number of trade names such as TEGADERM™ (3M Company, St. Paul, Minn.) and OP-SITE™ (Smith & Nephew, Hull, England).

The polymeric films used in those dressings and drapes are conformable, i.e., the films are extremely thin, flexible and supple. They are typically supplied with a releasable protective liner covering the adhesive coated surface of the film. When the liner is removed, the adhesive coated film tends to wrinkle and adhere to itself, interfering with the smooth, aseptic application of the dressing to a patient's skin. Various delivery systems have been proposed to address this problem such as those disclosed in U.S. Pat. No. 6,685,682. The use of a removable carrier, which does not require tearing of the film after it has been placed on the patient, avoids the problems described above. The carrier also aids in accurate placement of the dressing on a patient.

Thin polymeric films that are flexible and resilient are beneficial when used on skin that flexes, stretches, and retracts. However, for some application, like when securing devices such as tubing, ports, and catheters, the high flexibility and resiliency of the thin polymeric film can cause too much movement of the secured medical device. Therefore, medical dressings have been developed that further incorporate areas having secured to the thin polymeric film, stiffer, less conformable materials such as adhesives, films, or fabrics. For example, U.S. Pat. No. 5,088,483 discloses an adhesive composite that includes a conformable backing and a permanent adhesive reinforcement around the periphery of the adhesive composite. One example of a commercially available medical dressing with a reinforcement layers is TEGADERM™ IV Advanced Dressing (3M Company, St. Paul Minn.).

In some instances medical dressings are applied to a patient and remain in place for several days. When dressings are worn over time, the edge of the dressing can begin to peel away from the patient possibly resulting in contamination at the site or adhesive failure entirely. The use of less resilient materials to add stiffness and less flexibility to areas of the dressing can contribute to adhesive failure of the dressing on skin. When the skin flexes and stretches, but the less resilient material cannot, then the adhesive will pull away from the skin. A need remains for a medical dressing that can strongly secure to skin, while also being highly flexible and conformable over skin.

SUMMARY

The disclosed medical dressing is highly flexible and conformable over skin, while maintaining strong adhesive securement to skin over extended periods of time. The dressing comprises a backing layer, support material, and a plurality of specifically placed slits in the support material, which allow for stretching and recovery of the backing layer.

In one embodiment, the medical dressing comprises a first major surface, second major surface, opposite the first major surface, and a perimeter, wherein the second major surface comprises an adhesive. The dressing comprises a backing layer that is elastic, a support material secured to the backing layer that is less elastic than the backing layer, a plurality of slits through the support material, wherein each slit is a long narrow through cut in the support material, and wherein each slit is spaced from an adjacent slit.

"Elastic" means a material able to elongate and regain some or all of its original shape.

"Slit" means a long, narrow through cut. In one embodiment, the slit has a length that is significantly longer that a width. In one embodiment, the slit has a length at least 5 times greater than a width. In one embodiment, the slit has a length at least 10 times greater than a width. In one embodiment, the slit has essentially no width.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments.

As used herein, "a," "an," "the," "at least one," and "one or more" are used interchangeably. The term "and/or" (if used) means one or all of the identified elements or a combination of any two or more of the identified elements.

While the above-identified drawings and figures set forth embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of this invention.

The figures may not be drawn to scale.

DETAILED DESCRIPTION

Figure 1:
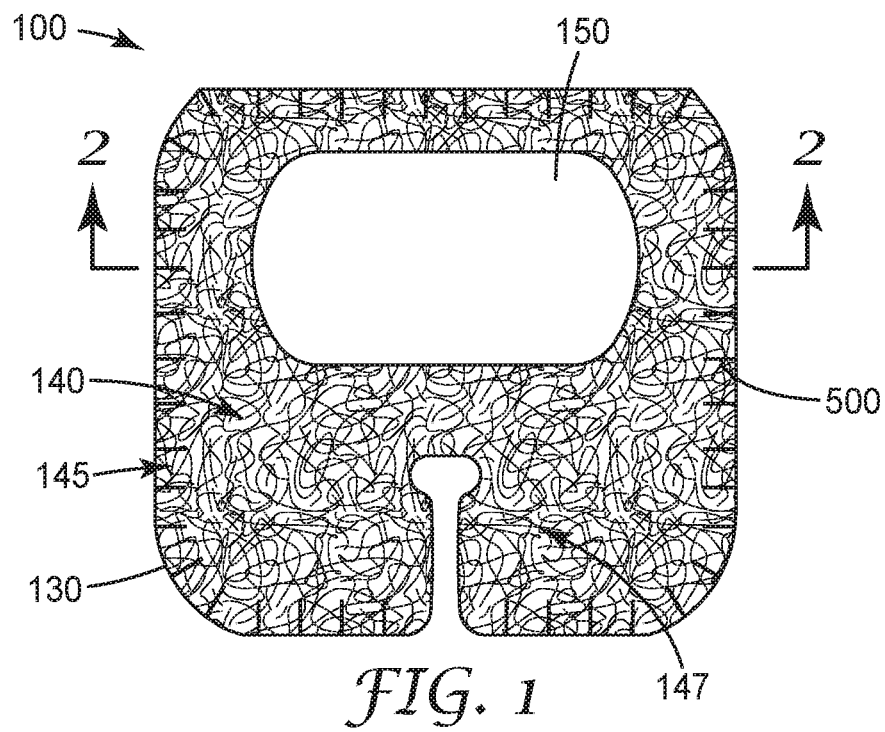
FIG. 1 is a first embodiment of a medical dressing comprising a plurality of slits.

FIG. 1 is a first embodiment of a medical dressing 100 comprising a plurality of slits 500. The medical dressing shown in FIG. 1 is a dressing used to cover the site of an inserted intravenous catheter. Overall, the medical dressing 100 has a first major surface 110 and second major surface 120, which is opposite the first major surface 110. At least a portion of the second major surface 120 comprises an adhesive 200. A perimeter 130 surrounds the medical dressing 100 and defines a dressing area 140.

The medical dressing 100 has a backing layer 300 and a support material 400 that is secured to the backing layer 300. Through at least the support material 400 are a plurality of slits 500. In FIG. 1 and in the other images, the slits 500 are depicted as a relatively thick black line so as to clearly communicate the location of the slit 500 on the dressing 100. It is understood that the slit 500 can be simply a through cut and therefore not having the thickness as depicted in these images.

Figure 2:
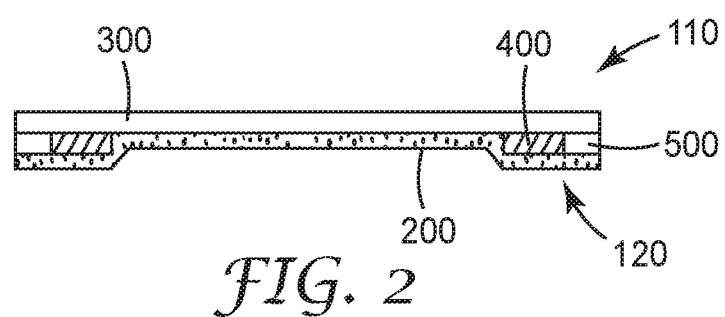
FIG. 2 is a side sectional view of FIG. 1 through line 2-2.

FIG. 2 is a side sectional view of FIG. 1 through line 2-2. In this embodiment, the backing layer 300 forms the first major surface 110. In this embodiment, the support material 400 extends adjacent the entire perimeter 130, but is not continuous across the entire dressing area 140. As best seen in FIGS. 1 and 2, the support material 400 is not located in a central window 150 of the medical dressing 100, which allows for a transparent window to view the inserted catheter. It is both the backing layer 300 and the support material 400 making up the second major surface 120. In this embodiment, the adhesive 200 covers the entire second major surface 120.

It is understood that the adhesive 200 may cover only a portion of the second major surface 120. For example, in the embodiment shown in FIG. 1-3, the adhesive 200 may cover only the portion of the second major surface 120 having the support material 400, which would be the portion adjacent the perimeter.

FIG. 2 shows the backing layer 300 at the first major surface 110, while the support material 400 is at the second major surface 120. In one embodiment, the support material 400 may be at the first major surface 110 and the backing layer 300 at the second major surface 120. It is understood that one or more additional layers may be included adjacent the backing layer 300, support material 400, between the backing layer 300 and support material 400.

Figure 3:
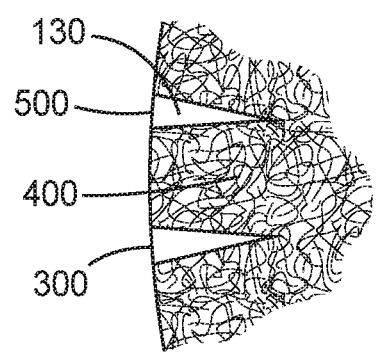
FIG. 3 is an enlarged top view of the medical dressing of FIG. 1, showing the stretching of the dressing at several slits.

Generally, the backing layer 300 will extend over the entire dressing area 140 as it is the portion of the dressing 100 that provides a barrier against external contamination to the underlying substrate. The support material 400 is shown in the embodiment of FIGS. 1-3 covering only a portion of the dressing area 140; however, in other embodiments the support material 400 may cover nearly the entire dressing area 140.

The sectional view of FIG. 2 passes directly through slits 500. As can be seen in FIG. 2, the slits 500 are only in the support material and extend from the perimeter 140 into a portion of the dressing area 140. The slit 500 does not entirely transverse the support material. Each slit 500 is separate from, and disconnected from another adjacent slit 500.

The backing layer 300 is elastic and a sufficiently impermeable barrier to the passage of liquids and at least some gases, which protects the covered site from external contaminants. Being elastic allows for the backing layer 300 to expand, contract, stretch and recover as the underlying substrate, such as skin, moves.

Elasticity can be measured in any number of commonly used means for evaluating stretch and recovery of a material. In one embodiment, the backing layer 300 (independent of the support material) has an elongation to break of at least 200%. In one embodiment, the backing layer 300 (independent of the support material) has an elongation to break of less than 500%. In one embodiment, the support material 400 (independent of the backing layer) has an elongation to break of at least 20%. In one embodiment, the support material 400 (independent of the backing layer) has an elongation to break of at least 100%. In one embodiment, the support material 400 has an elongation to break less than 200%.

Elasticity can be measured by an initial modulus of elasticity, which is the force require to apply a specified amount of stretch. In one embodiment, the backing layer 300 has a modulus, at 10% elongation, of less than 2 Newtons. In one embodiment, the backing layer 300 has a modulus, at 10% elongation, of less than 1.5 Newtons. In one embodiment, when the support material 400 is secured with the backing layer 300 in the first portion with slits 500, the modulus at 10% elongation is less than 2 Newtons. In one embodiment, when the support material 400 is secured with the backing layer 300 in the first portion with slits 500, the modulus at 10% elongation is less than 1 Newton. In one embodiment, when the support material 400 is secured with the backing layer 300 in the second portion without slits, the modulus at 10% elongation is greater than 1 Newton and less than 6 Newtons. In one embodiment, when the support material 400 is secured with the backing layer 300 in the second portion without slits, the modulus at 10% elongation is greater than 2 Newton and less than 5 Newtons. In one embodiment, when the support material 400 is secured with the backing layer 300, the ratio of the modulus at 10% elongation of the second portion without slits to the modulus at 10% of the first portion with slits is at least 2:1. In one embodiment, when the support material 400 is secured with the backing layer 300, the ratio of the modulus at 10% elongation of the second portion without slits to the modulus at 10% of the first portion with slits is at least 4:1. In one embodiment, when the support material 400 is secured with the backing layer 300, the ratio of the modulus at 10% elongation of the second portion without slits to the modulus at 10% of the first portion with slits is at least 6:1.

The support material 400 is secured to the backing layer 300, through adhesive, thermal bonding, lamination, or other commonly used securement techniques. The support material 400 provides structural strength to the medical dressing 100, and therefore, independently, is less elastic that the backing layer 300. In one embodiment, the support material, independently, has essentially no elasticity, such that is may be unable to stretch and/or it may be unable to recover from a stretch. In one embodiment, the support material, may be more elastic in one direction (machine direction) than in the cross direction (transverse direction), but overall is has less elasticity than the backing layer 300.

FIG. 3 is an enlarged top view of the medical dressing 100 of FIGS. 1 and 2, showing the stretching of the dressing 100 at several slits 500. When the dressing 100 is subject to elongation, the elastic backing layer 300 will stretch, but the less elastic support material 400 is less able to stretch or recover. However, the slits 500 allow the support material 400 to extend and therefore allow for elongation of the backing layer 300 at the slit, which can be seen in FIG. 3. The elasticity of the backing layer 300, when recovering from the stretch, will also recover the attached support material 400, returning the dressing 100 much to the configuration as shown in FIG. 1. Therefore, the slits allow for control of the stretch and recovery of discrete areas of the support material.

In some circumstances, more stretching occurs at the perimeter 130 of the dressing. Therefore, in the embodiment shown in FIG. 1, the plurality of slits 500 are located along at least a portion of the perimeter 130 of the dressing 100. The slits 500 at the perimeter 130 begin directly at the perimeter 130 and extend partially in to the support material 400. In this embodiment, the slits 500 are located along the entire perimeter 130. The slits 500 may have a variety of sizes or shapes, and it is understood that each slit can have a size and shape the same as or different from the other slits 500 on the dressing 100.

In one embodiment, the slits 500 are at least 1 mm in length. In one embodiment, the slits 500 are at least 5 mm in length. In one embodiment, the slits are less than 5 cm in length. In one embodiment, the slits are less than 1 cm in length.

In one embodiment, such as shown in FIG. 1, the slits 500 are a through cut in the support material and have essentially no width, meaning that no material was removed from the support material during cutting. In one embodiment, the slits have a width less than 5 mm. In one embodiment the slits have a width less than 1 mm.

In one embodiment, the slits 500 at the perimeter 130 are shown extending in a straight line inward, generally perpendicular to the part of the perimeter 130 it is understood that any shape or placement of the slits 500 at the perimeter could achieve the same purpose of allowing expansion and contraction of the backing layer 300 at the perimeter 130.

In the embodiment shown in FIGS. 1-3 the slits 500 are only through the support material 400. It is understood that depending on the particular arrangement of layers or the particular application of the dressing the slit 500 may extend to both the backing layer and support material 400.

Selectively placed slits 500 allow for some portions of the medical dressing 100 to have more elasticity than portions of the dressing 100 with the support material 400 that do not have the slits 500. For example, in the embodiment shown in FIG. 1-3, the dressing area 140 has a first portion 145 adjacent the perimeter 130 with slits that have more elasticity than a second portion 147 of the dressing area 140 having support material 400 but without slits 500. This is desirable as underlying medical devices or tubing at the second portion 147 should not be allowed to stretch as much as portions of the dressing 100 at the perimeter 130.

If the support material 400 did not have slits, when the dressing 100 is subject to elongation, the elastic backing layer 300 will stretch, but the less elastic support material 400 is less able to stretch or recover. Therefore, if the underlying substrate, for example skin, continues to stretch beyond the ability of the support material 400 to stretch, then the adhesion between the adhesive 200 and the underlying substrate will begin to break. In some circumstances, more stretching occurs at the perimeter 130 of the dressing. When the adhesion breaks at the perimeter, then the edges of the dressing begin to lift away from the skin.

Reference to similar structural components from one embodiment to another will use the same reference numbers. Unless noted otherwise, description applicable from one embodiment has applicability to other similar embodiments.

Figure 4:
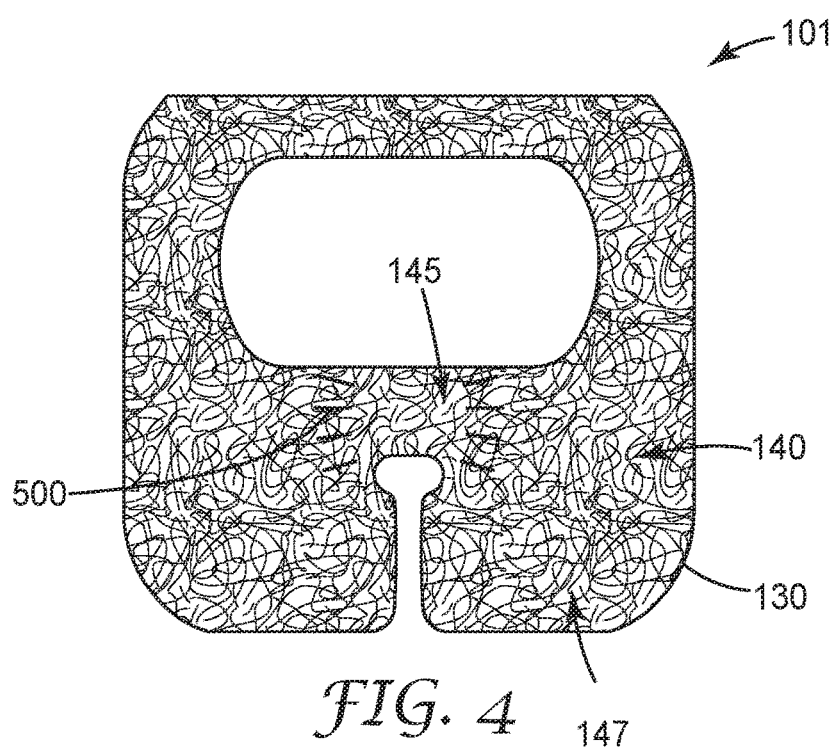
FIG. 4 is a second embodiment of a medical dressing comprising a plurality of slits.

FIG. 4 is a second embodiment of a medical dressing 101 comprising a plurality of slits 500 within in dressing area 140. In this embodiment, the dressing area 140 includes a first portion 145 having the plurality of slits 500, and a second portion 147 with support material 400 without slits. The arrangement of slits 500 is generally radially outward from the first portion 145 so that there is a pocket that can form when the support material 400 and attached backing layer 300 are allowed to stretch. The location of the first portion 145 of the dressing area, containing the slits 500 coincides with the location of an underlying medical devices or tubing. As described with respect to FIGS. 1-3, the slits 500 allow for expansion of the support material, while the barrier layer stretches to better conform with the underlying medical device or tubing, while the strength of the support material still prevents excessive stretching and movement of the medical device or tubing.

It is understood that a single dressing may include one or more select areas that may each have a plurality of slits 500. For example, a single dressing may have an arrangement of slits 500 within the dressing area 140 such as shown in FIG. 4 and an arrangement of slits 500 at the perimeter 130 such as shown in FIG. 1.

Figure 5:
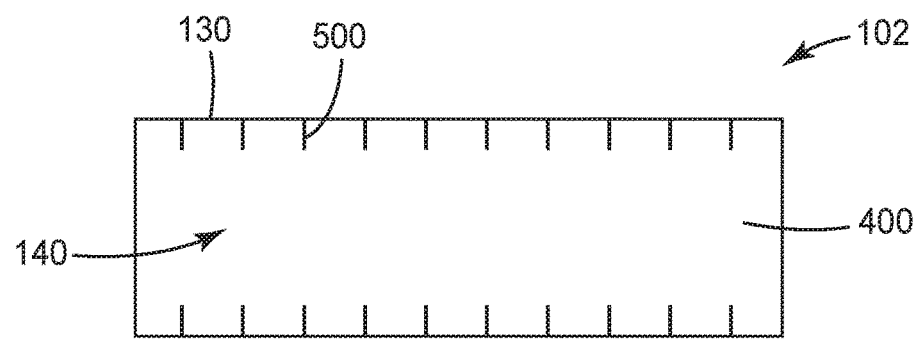
FIG. 5 is a third embodiment of a medical dressing, specifically a tape, comprising a plurality of slits.

FIG. 5 is a third embodiment of a medical dressing 102, specifically a tape, comprising a plurality of slits 500. In this embodiment, the plurality of slits 500 extend along opposing portions of the longitudinally extending sides of the perimeter 130. In this embodiment, the support material 400 covers the entire dressing area 140. As with other embodiments, each slit 500 is separate from an adjacent slit 500. The slits 500 at opposing portions of the longitudinally extending sides of the perimeter 130 may or may not align with one another. This arrangement of slits 500 allows for improved stretching and recovery in a direction along the longitudinally extending medical dressing 102.

Figure 6:
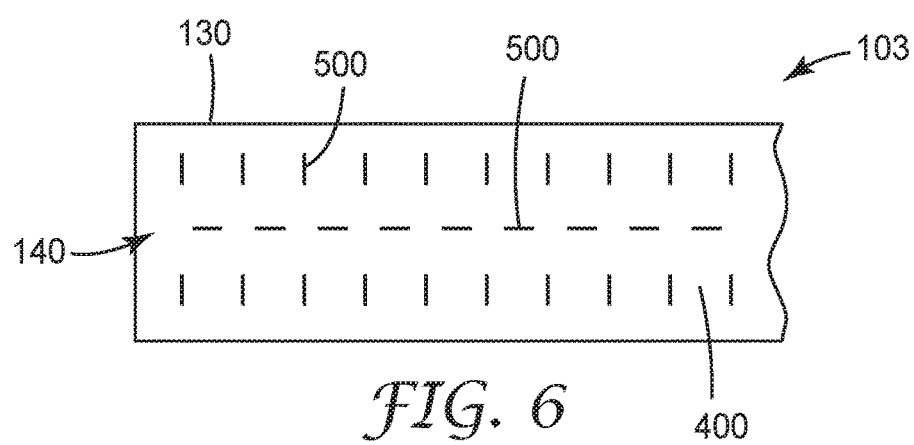
FIG. 6 is a fourth embodiment of a medical dressing, specifically a tape, comprising a plurality of slits.

FIG. 6 is a fourth embodiment of a medical dressing 103, specifically a tape, comprising a plurality of slits 500. In this embodiment, the plurality of slits 500 extend throughout the entire dressing area 140. Some slits 500 are arranged perpendicular to other slits. Therefore, this dressing will allow for improved stretching and recover in a direction along the longitudinally extending medical dressing 103, as well as perpendicular to the longitudinally extending medical dressing 103. For either embodiment shown in FIGS. 5 and 6, it is understood that the tape could be provided in a variety of shapes and sizes of precut tape sections or the tape may be an elongated, longitudinally extending tape that could be provided in roll form.

The medical dressing disclosed may be made by conventional techniques (e.g., extrusion, solvent casting, calendaring, laminating, adhesive coating, and the like) which are familiar to those skilled in the art. U.S. Pat. No. 6,685,682, the disclosure of which is herein incorporated by reference, discloses constructions and methods for making medical dressings with backing layers and support material. It will be understood that the slits can be applied during the rotary converting process.

Backing Layer

The medical dressings are useful to provide an impermeable barrier to the passage of liquids and at least some gases. Representative barriers may include non-woven and woven fibrous webs, knits, films, foams polymeric films and other familiar backing materials. In some embodiments, a transparent substrate is desirable to allow for viewing of the underlying skin or medical device.

In one embodiment, the substrate has high moisture vapor permeability, but generally impermeable to liquid water so that microbes and other contaminants are sealed out from the area under the substrate. One example of a suitable material is a high moisture vapor permeable film such as described in U.S. Pat. Nos. 3,645,835 and 4,595,001, the disclosures of which are herein incorporated by reference. In high moisture vapor permeable film/adhesive composites, the composite should transmit moisture vapor at a rate equal to or greater than human skin such as, for example, at a rate of at least 300 g/m²/24 hrs at 37° C./100-10% RH, or at least 700 g/m²/24 hrs at 37° C./100-10% RH, or at least 2000 g/m²/24 hrs at 37° C./100-10% RH using the inverted cup method as described in U.S. Pat. No. 4,595,001. Perforated substrates or films or pattern coated adhesives may be used to increase the moisture vapor transmission. In one embodiment, the substrate is an elastomeric polyurethane, polyester, or polyether block amide films. These films combine the desirable properties of resiliency, elasticity, high moisture vapor permeability, and transparency. A description of this characteristic of backing layers can be found in issued U.S. Pat. Nos. 5,088,483 and 5,160,315, the disclosures of which are hereby incorporated by reference Commercially available examples of potentially suitable backing materials may include the thin polymeric film backings sold under the trade names TEGADERM (3M Company), OPSITE (Smith & Nephew), etc. Many other backings may also be used, including those commonly used in the manufacture of surgical incise drapes (e.g., incise drapes manufactured by 3M Company under the trade names STERIDRAPE and IOBAN), etc.

Because fluids may be actively removed from the sealed environments defined by the medical dressings, a relatively high moisture vapor permeable backing may not be required. As a result, some other potentially useful backing materials may include, e.g., metallocene polyolefins and SBS and SIS block copolymer materials could be used.

Regardless, however, it may be desirable that the backing be kept relatively thin to, e.g., improve conformability. For example, the backing layer may be formed of polymeric films with a thickness of 200 micrometers or less, or 100 micrometers or less, potentially 50 micrometers or less, or even 25 micrometers or less.

Support Material

The support material provides strength to the thin, flexible backing layer. The support material therefore has more stiffness and less elasticity than the backing layer. The support material may be a coating, such as an adhesive, or may be a self-supporting substrate such as another film, woven, knitted, or nonwoven fabric. For example, U.S. Pat. No. 5,088,483 discloses a permanent adhesive as a reinforcement that could be used as the support material.

One example of nonwoven for the support material is a high strength nonwoven fabric available from E. I. Dupont de Nemours & Company of Wilmington, Del. under the trademark Sontara, including Sontara 8010, a hydroengangled polyester fabric. Other suitable nonwoven webs include a hydroentangled polyester fabric available from Veratec, a division of International Paper of Walpole, Mass. Another suitable nonwoven web is the nonwoven elastomeric web described in U.S. Pat. No. 5,230,701, herein incorporated by reference.

Adhesive

Suitable adhesive for use in wound dressing articles include any adhesive that provides acceptable adhesion to skin and is acceptable for use on skin (e.g., the adhesive should preferably be non-irritating and non-sensitizing). Suitable adhesives are pressure sensitive and in certain embodiments have a relatively high moisture vapor transmission rate to allow for moisture evaporation. Suitable pressure sensitive adhesives include those based on acrylates, urethanes, hyrdogels, hydrocolloids, block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent.

The pressure sensitive adhesives that may be used in the wound dressings may include adhesives that are typically applied to the skin such as the acrylate copolymers described in U.S. Pat. No. RE 24,906, particularly a 97:3 isooctyl acrylate:acrylamide copolymer. Another example may include a 70:15:15 isooctyl acrylate: ethyleneoxide acrylate: acrylic acid terpolymer, as described in U.S. Pat. No. 4,737,410 (Example 31). Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

Silicone adhesive can also be used. Generally, silicone adhesives can provide suitable adhesion to skin while gently removing from skin. Suitable silicone adhesives are disclosed in PCT Publications WO2010/056541 and WO2010/056543, the disclosure of which are herein incorporate by reference.

The pressure sensitive adhesives may, in some embodiments, transmit moisture vapor at a rate greater to or equal to that of human skin. While such a characteristic can be achieved through the selection of an appropriate adhesive, it is also contemplated that other methods of achieving a high relative rate of moisture vapor transmission may be used, such as pattern coating the adhesive on the backing, as described in U.S. Pat. No. 4,595,001. Other potentially suitable pressure sensitive adhesives may include blown-micro-fiber (BMF) adhesives such as, for example, those described in U.S. Pat. No. 6,994,904. The pressure sensitive adhesive used in the wound dressing may also include one or more areas in which the adhesive itself includes structures such as, e.g., the microreplicated structures described in U.S. Pat. No. 6,893,655.

Issued U.S. Pat. Nos. 3,645,835 and 4,595,001, the disclosures of which are hereby incorporated by reference, describe methods of making such films and methods for testing their permeability. Preferably, the film/adhesive composite should transmit moisture vapor at a rate equal to or greater than human skin. Preferably, the adhesive coated film transmits moisture vapor at a rate of at least 300 g/m²/24 hrs/37 C/100-10% RH, more preferably at least 700 g/m²/24 hrs/37 C/100-10% RH, and most preferably at least 2000 g/m²/24 hrs/37 C/100-10% RH using the inverted cup method as described in U.S. Pat. No. 4,595,001.

Different portions of the dressing may include different adhesives, such as disclosed in U.S. Patent Application 61/664,246 filed Jun. 26, 2012 titled "Medical Dressing with Multiple Adhesives." For example, a portion may include an acrylate adhesive while another portion may include a silicone adhesive. In one embodiment, to prevent edge separation, adjacent the perimeter is acrylate adhesive, while near the central portion there is silicone adhesive. In one embodiment, to strongly secure with a device or tubing near the central portion there is acrylate adhesive, while near the perimeter in contact with skin is silicone adhesive.

Optional Components

An absorbent material may also be used in conjunction with the medical dressings described herein. An absorbent material may be the same as the wound packing material (described below) or may be a separate element. The absorbent materials can be manufactured of any of a variety of materials including, but not limited to, woven or nonwoven cotton or rayon. Absorbent pad is useful for containing a number of substances, optionally including antimicrobial agents, drugs for transdermal drug delivery, chemical indicators to monitor hormones or other substances in a patient, etc.

The absorbent may include a hydrocolloid composition, including the hydrocolloid compositions described in U.S. Pat. Nos. 5,622,711 and 5,633,010, the disclosures of which are hereby incorporated by reference. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X4ink CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B.F. Goodrich, Brecksville, Ohio), or a combination thereof. Absorbent materials may also be chosen from other synthetic and natural hydrophilic materials including polymer gels and foams.

An optional release liners may be included that covers all or a portion of the adhesives to prevent contamination of the adhesives. In one embodiment, the package that contains the adhesive dressing may serve as a release liner. Suitable release liners can be made of kraft papers, polyethylene, polypropylene, polyester or composites of any of these materials. In one embodiment, the liners are coated with release agents such as fluorochemicals or silicones. For example, U.S. Pat. No. 4,472,480, the disclosure of which is hereby incorporated by reference, describes low surface energy perfluorochemical liners. In one embodiment, the liners are papers, polyolefin films, or polyester films coated with silicone release materials.

An optional carrier may be included that covers all or a portion of the first major surface of the substrate, providing structural support if the dressing is thin and highly flexible. The carrier maybe removable from the first major surface once the adhesive dressing is placed on skin. The carrier can be constructed of a variety of materials such as fabric that are woven or kitted, nonwoven material, papers, or film. In one embodiment, the carrier is along the perimeter of the first major surface of the dressing and is removable from the first major surface, similar to the carrier used the 3M Tegaderm™ Transparent Film Dressing, available from 3M Company, St. Paul, Minn.

An optional antimicrobial component may be included that is either separate from the adhesive dressing or may be integral with the dressing. The antimicrobial component is placed near or adjacent to the insertion site of the medical device to inhibit microbial growth in and around the insertion site. The antimicrobial component can be absorbent foam or gel, such as used in a 3M Tegaderm™ CHG I.V. Securement Dressing, available from 3M Company.

Although specific embodiments of this invention have been shown and described herein, it is understood that these embodiments are merely illustrative of the many possible specific arrangements that can be devised in application of the principles of the invention. Numerous and varied other arrangements can be devised in accordance with these principles by those of ordinary skill in the art without departing from the spirit and scope of the invention. Thus, the scope of the present invention should not be limited to the structures described in this application, but only by the structures described by the language of the claims and the equivalents of those structures.

What is claimed is:

1. A medical dressing comprising: a first major surface, a second major surface opposite the first major surface, and a perimeter, wherein the second major surface comprises an adhesive;
    a backing layer adjacent the first major surface that is elastic and moisture-vapor permeable and water impermeable;
    a support material secured to the backing layer adjacent, the second major surface that is less elastic than the backing layer, wherein the support material extends adjacent the entire perimeter but is not continuous across the entire dressing;
    a plurality of slits through the support material extending from the perimeter, wherein each slit is a long narrow through cut in the support material, having essentially no width between the support material on either side of the through cut, and wherein each slit is spaced from an adjacent slit;
    wherein, when the medical dressing is subject to elongation at each slit, the elastic backing layer stretches, and the less elastic support material at extends to widen each slit.

2. The medical dressing of claim 1, wherein the perimeter forms a dressing area, and wherein the plurality of slits are at a first portion of the dressing area and a second portion of the dressing area is free of slits.

3. The medical dressing of claim 2, wherein the first portion of the dressing area comprising the plurality of the slits has an elasticity greater than the second portion of the dressing area that is free of any slits.

4. The medical dressing of claim 2, wherein the plurality of slits at the first portion of the dressing area comprise slits extending radially from the first portion of the dressing area.

5. The medical dressing of claim 1, wherein the ratio of the modulus at 10% elongation of a second portion without slits to the modulus at 10% elongation of a first portion with the plurality slits is at least 2:1.

6. The medical dressing of claim 5, where the modulus at 10% elongation of the first portion with slits is less than 2 Newtons.

7. The medical dressing of claim 1, wherein the adhesive covers only a portion of the second major surface.

8. The medical dressing of claim 1, wherein the backing layer is at the first major surface.

9. The medical dressing of claim 1, wherein the backing layer, (independently) has an elongation to break of 200% to 500% and the support layer (independently) has an elongation to break of less than 200%.

10. The medical dressing of claim 1, wherein the plurality of slits are in the support material and backing layer.

11. The medical dressing of claim 1, wherein a first portion of the plurality of slits are parallel to one another and a second portion of the plurality of slits are parallel to one another but perpendicular to the first portion of the plurality of slits.

12. The medical dressing of claim 1, wherein the plurality of slits are adjacent the perimeter of the medical dressing.

13. The medical dressing of claim 1, wherein the plurality of slits directly contact a portion of the perimeter and extend from the perimeter inward to the medical dressing.

14. The medical dressing of claim 1, wherein the plurality of slits are only adjacent a portion of the perimeter of the medical dressing directly contacting the perimeter and extending from the perimeter inward to the medical dressing.

15. The medical dressing of claim 1, wherein each slit has a length that is at least 5 times greater than the width of the slit.

16. The medical dressing of claim 1, further comprising an absorbent material recessed from the perimeter.

17. The medical dressing of claim 1, wherein the backing layer is transparent.

18. The medical dressing of claim 1, wherein the backing layer is generally impermeable to liquid and can transmit moisture vapor at a rate of at least 300 g/m$^2$/24 hrs at 37° C./100-10% RH.

19. The medical dressing of claim 1, wherein the backing layer continuously overlies the support material at the plurality of slits.

* * * * *

UNITED STATES PATENT AND TRADEMARK OFFICE
CERTIFICATE OF CORRECTION

PATENT NO. : 10,940,049 B2
APPLICATION NO. : 14/773956
DATED : March 9, 2021
INVENTOR(S) : Steven Heinecke Page 1 of 1

It is certified that error appears in the above-identified patent and that said Letters Patent is hereby corrected as shown below:

In the Specification

Column 1
Line 27, Delete "OP-SITE™" and insert -- OPSITE™ --, therefor.

Column 3
Line 31, Delete "FIG." and insert -- FIGS. --, therefor.

Column 5
Line 38, Delete "FIG." and insert -- FIGS. --, therefor.

Column 7
Line 14, After "reference" insert -- . --.

Column 7
Line 22, Delete "STERIDRAPE" and insert -- STERI-DRAPE --, therefor.

Column 7
Line 48-49, Delete "hydroengangled" and insert -- hydroentangled --, therefor.

Column 7
Line 64, Delete "hyrdogels," and insert -- hydrogels, --, therefor.

In the Claims

Column 10
Line 9, Claim 1, delete "adjacent," and insert -- adjacent --, therefor.

Column 10
Line 23, Claim 1, after "material" delete "at".

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*